United States Patent
Wanezaki et al.

(10) Patent No.: US 7,560,131 B2
(45) Date of Patent: *Jul. 14, 2009

(54) HIGH SOLUBILITY COMPOSITION WITH HIGH ISOFLAVONE CONCENTRATION AND PROCESS OF PRODUCING SAME

(75) Inventors: Satoshi Wanezaki, Izumisano (JP); Hideo Araki, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 786 days.

This patent is subject to a terminal disclaimer.

(21) Appl. No.: 10/540,065

(22) PCT Filed: Dec. 22, 2003

(86) PCT No.: PCT/JP03/16508

§ 371 (c)(1), (2), (4) Date: Jun. 22, 2005

(87) PCT Pub. No.: WO2004/057983

PCT Pub. Date: Jul. 15, 2004

(65) Prior Publication Data

US 2007/0003642 A1    Jan. 4, 2007

(30) Foreign Application Priority Data

Dec. 24, 2002   (JP)  ............................. 2002-372581

(51) Int. Cl.
*A23L 1/20* (2006.01)
(52) U.S. Cl. .................. 426/634; 426/426; 426/428; 426/429; 426/430
(58) Field of Classification Search ................ 426/634, 426/426, 428, 429, 430
See application file for complete search history.

(56) References Cited

U.S. PATENT DOCUMENTS

| | | | |
|---|---|---|---|
| 5,789,581 A | * | 8/1998 | Matsuura et al. ............ 536/128 |
| 6,399,072 B1 | | 6/2002 | Empie et al. |
| 7,108,871 B2 | * | 9/2006 | Bombardelli et al. ....... 424/757 |

FOREIGN PATENT DOCUMENTS

| | | | |
|---|---|---|---|
| JP | 61-129134 | * | 6/1986 |
| JP | 62-5917 | * | 1/1987 |
| JP | 62-126186 | | 6/1987 |
| JP | 4-266898 | | 9/1992 |
| JP | 8-283283 | | 10/1996 |
| JP | 10-298175 | | 11/1998 |
| JP | 2000-50839 | | 2/2000 |
| JP | 2000-327692 | | 11/2000 |
| JP | 2002-80474 | | 3/2002 |

OTHER PUBLICATIONS

Shirawiwa et al. Composition and STructure of "Group A Saponin" in Soybean Seed. Agric. Biol. Chem., 55(2) pp. 315-322. 1991.*

* cited by examiner

*Primary Examiner*—Anthony Weier
(74) *Attorney, Agent, or Firm*—Wenderoth, Lind & Ponack, L.L.P.

(57) ABSTRACT

It is intended to provide a composition containing isoflavones which has a high purity and yet is highly soluble in water in a natural state without adding any solubilizers or subjecting to chemically modification. It is found out that a composition containing isoflavones with a high purity and a high solubility in water can be obtained by extracting soybean hypocotyls with a water-containing alcohol within a specific temperature range, then allowing a synthetic adsorbent resin to adsorb the obtained extract and eluting with a water-containing alcohol at a specific concentration.

6 Claims, No Drawings

HIGH SOLUBILITY COMPOSITION WITH HIGH ISOFLAVONE CONCENTRATION AND PROCESS OF PRODUCING SAME

TECHNICAL FIELD

The present invention relates to an isoflavone-containing composition which is highly soluble in water although which has high purity, and a process for producing the composition.

BACKGROUND ART

Isoflavones found in soybeans mainly include free isoflavone glycosides such as daidzin, genistin and glycitin; malonyl isoflavone glycosides such as 6"-O-malonyl daidzin, 6"-O-malonyl genistin and 6"-O-malonyl glycitin; acetyl isoflavone glycosides such as 6"-O-acetyl daidzin, 6"-O-acetyl genistin and 6"-O-acetyl glycitin; and isoflavone aglycones such as daidzein, genistein and glycitein.

Isoflavones are active constituents of soybeans which have various activities such as alleviation of osteoporosis and climacteric disturbance, and have been widely used, for example, as an additive for health foods. Accordingly, various methods for extracting and purifying isoflavones have been devised in order to efficiently ingest isoflavones.

JP-A 62-126186 (the patent document 1) discloses a method comprising extracting soybean broth or soybeans with an aqueous organic solvent under reflux to obtain an extract, bringing the extract into contact with a synthetic adsorbent resin such as a styrene-divinylbenzene polymeric resin, and then eluting isoflavones from the resin with an aqueous organic solvent (for example, ethanol or 70% methanol). In the patent document 1, although there is no detailed explanation about the concentration of an aqueous organic solvent used for extraction, 80% aqueous ethanol is used in Example 2. However, the objective of the patent document 1 is to obtain a large quantity of isoflavones at low cost, and no attention is paid to the solubility of the resulting composition in water.

JP-A 8-283283 (the patent document 2) discloses a method for purifying malonyl isoflavone glycosides comprising extracting soybeans with water to obtain an extract, bringing the extract into contact with a synthetic adsorbent resin, and then eluting the isoflavone glycosides from the resin with, for example, 20-50% aqueous ethanol. The patent document 2 states that the suitable extraction temperature is 45 to 65° C. The objective of the patent document 2 is to purify malonyl isoflavone glycosides that are relatively high hydrophilic. However, the extraction rate of the isoflavones is low because of extraction with water, and thus a composition containing a high concentration of isoflavones can not be obtained. In addition, there is no description with respect to the solubility of the resulting composition in water.

The compositions obtained by the methods described in the patent documents 1 and 2 contain a low concentration of isoflavones and do not have satisfactory solubility in water.

JP-A 2002-80474 (the patent document 3) discloses a method for obtaining a free isoflavone glycoside fraction comprising extracting soybean hypocotyls with aqueous lower alcohol (for example, 70% ethanol) at room temperature to 80° C. to obtain an extract, bringing the extract into contact with an anion exchange resin having a uniform particle diameter, washing the resin with water, and then eluting free isoflavone glycosides from the resin with, for example, 70% aqueous ethanol. The composition obtained by purification with the anion exchange resin contains isoflavones at high concentration, namely, 60% or more. However, the composition is poorly soluble in water because it is a purified product of free isoflavone glycosides having a low solubility, and thus it has a problem of instability in an aqueous solution.

Accordingly, the methods described in the patent documents 1 to 3 can not provide a composition containing a high concentration of isoflavones and having a high solubility, which can be added into beverage.

Such problem arises from the low solubility of isoflavones themselves. For example, the solubility of daidzin is only about 3.3 mg/100 ml. JP-A 10-298175 (the patent document 4) discloses a method for improving the solubility of isoflavones in water which comprises extracting soybean hypocotyls with 70 to 90% aqueous alcohol at about 70° C. under reflux to obtain an extract, bringing the extract into contact with a synthetic adsorbent resin, eluting the resin with 30 to 80% aqueous alcohol to obtain an isoflavone-containing composition, and then forming an inclusion compound of the isoflavone-containing composition with cyclodextrin. Since this method requires an addition of at least an equimolar amount of cyclodextrin to the isoflavone extract, the isoflavone content in the final product is extremely decreased. Moreover, since the solubility of the final product depends on the solubility of cyclodextrin itself, a step of dissolving the inclusion compound by heating is needed when it is used, and further, it can not be dissolved at a higher concentration.

JP-A 2000-327692 (the patent document 5) discloses a method for increasing the solubility comprising formation of α-glycosyl isoflavones by an action of glycosyltransferase in the presence of an α-glycosyl saccharide compound. However, this method also has a problem of decrease in the isoflavone content because it requires an addition of at least an equimolar amount of the saccharide compound.

Accordingly, there has been a need for development of an isoflavone-containing composition which has high purity and can be stably dissolved in water at a high concentration in a natural state without using any solubilizing agents such as cyclodextrin or any additives such as saccharide compounds and thus is suitable to use in beverage and the like.

REFERENCES

The patent document 1: JP-A 62-126186
The patent document 2: JP-A 8-283283
The patent document 3: JP-A 2002-80474
The patent document 4: JP-A 10-298175
The patent document 5: JP-A 2000-327692

DISCLOSURE OF INVENTION

Problem to be Solved by the Invention:

The present invention is to provide a novel isoflavone-containing composition which has high solubility in water although which has high purity in a natural state without adding any solubilizing agents or without applying any chemical modifications, and a process for producing the isoflavone-containing composition.

Solution for the Problem:

The present inventors studied intensively and as a result, they prepared an isoflavone-containing composition containing malonyl isoflavone glycosides, isoflavones other than malonyl isoflavone glycosides and saponins in specified proportions from soybean hypocotyls, and then found that the isoflavone-containing composition surprisingly contained a high concentration of isoflavones and had remarkably high solubility. In addition, the present inventors found that the isoflavone-containing composition could be obtained by extracting soybean hypocotyls with aqueous alcohol within a specified temperature range, allowing the extract to be adsorbed to a nonpolar synthetic adsorbent resin, and then eluting the resin with aqueous alcohol having a specified alcohol concentration, as a particularly preferable process.

That is, the present invention discloses the following inventions:

(1) an isoflavone-containing composition which comprises 15 to 95% by weight of malonyl isoflavone glycosides, 0 to 50% by weight of isoflavones other than malonyl isoflavone glycosides and 5 to 60% by weight of saponins, by taking the sum of the total amounts of isoflavones and saponins in said composition as 100% by weight;

(2) the isoflavone-containing composition according to the above (1), which is prepared from soybean hypocotyls as the starting material;

(3) the isoflavone-containing composition according to the above (1), wherein the proportion of group A saponins in saponins is 55% by weight or more, by taking the total amount of saponins in said composition as 100% by weight;

(4) the isoflavone-containing composition according to the above (1), which has a water solubility of at least 20 mg/100 ml at 25° C. based on the amount of isoflavones;

(5) a process for producing the isoflavone-containing composition according to the above (2), which comprises the step of extracting soybean hypocotyls with 15 to 95% by volume aqueous ethanol at 10 to 50° C.;

(6) a process for producing the isoflavone-containing composition according to the above (2), which comprises the steps of:

(A) extracting soybean hypocotyls with 15 to 95% by volume aqueous ethanol at 10 to 50° C. to obtain an extract;

(B) bringing a solution of the extract obtained by the step (A) in water into contact with a nonpolar adsorbent resin to allow isoflavones to be adsorbed to the resin; and (C) eluting isoflavones from the adsorbent resin with 15 to 40% by volume aqueous ethanol;

(7) an edible composition containing the isoflavone-containing composition according to the above (1); and (8) a process for fractionating isoflavones and saponins, which comprises extracting soybean hypocotyls with 15 to 95% by volume aqueous ethanol at 10 to 50° C. to obtain an extract, bringing a solution of the extract in water into contact with a nonpolar adsorbent resin, eluting an isoflavone-containing fraction from the adsorbent resin with 15 to 40% by volume aqueous ethanol, and then eluting a saponin-containing fraction from the adsorbent resin with 65 to 90% by volume aqueous ethanol.

EFFECTS OF THE INVENTION

The present invention can provide an isoflavone-containing composition which has high solubility and contains a high concentration of isoflavones in a natural state without adding any solubilizing agents or without applying any chemical modifications, and said composition is highly soluble in water as compared with a conventional isoflavone-containing composition that has been considered to be readily soluble in water.

BEST MODE FOR CARRYING OUT THE INVENTION

The isoflavone-containing composition of the present invention preferably contains isoflavones in an amount of 25 to 95% by weight, more preferably 25 to 60% by weight, still more preferably 30 to 60% by weight, most preferably 40 to 60% by weight of the total solid content.

The isoflavone-containing composition of the present invention is characterized by the following three points, wherein the sum of the total amounts of isoflavones and saponins contained in said composition is defined as 100%:

1. the content of malonyl isoflavone glycosides is 15 to 95% by weight, more preferably 20 to 90% by weight, still more preferably 25 to 85% by weight, most preferably 30 to 80% by weight;

2. the content of isoflavones other than malonyl isoflavone glycosides (e.g., isoflavone glycosides, acetyl isoflavone glycosides, isoflavone aglycones and the like, i.e., the amount after subtracting the content of malonyl isoflavone glycosides from the total content of all isoflavones) is 0 to 50% by weight, more preferably 0 to 45% by weight, still more preferably 0 to 40% by weight, most preferably 0 to 30% by weight; and 3. the content of saponins is 5 to 60% by weight, more preferably 10 to 50% by weight, still more preferably 15 to 45% by weight, most preferably 20 to 40% by weight.

By using component percentages within the above-described ranges, an isoflavone-containing composition can be prepared, which has high solubility in water although which contains a high concentration of isoflavones, and which maintains high stability even under cold storage after dissolved.

The component percentages of the isoflavone-containing composition of the present invention are not particularly limited so long as they are within the above-described ranges. More specifically, the isoflavone-containing composition of the present invention may contain, in addition to isoflavones and saponins, 8 to 20% by weight of proteins based on the total solid content and may further contain saccharides. It is more preferable that the content of saponins is ¼ to ¾ times by weight the content of isoflavones.

Soybean saponins comprise group A saponins, group B saponins, group E saponins and the like. The appropriate proportion of group A saponins in saponins contained in the isoflavone-containing composition of the present invention is at least 55% by weight, more preferably at least 60% by weight, by taking the total amount of saponins in said composition as 100% by weight.

In the isoflavone-containing composition of the present invention, the solubility of isoflavones in water at 25° C. is at least 20 mg/100 ml, preferably 50 to 1200 mg/100 ml, more preferably 100 to 1200 mg/100 ml, still more preferably 500 to 1200 mg/100 ml. The isoflavone-containing composition of the present invention is not only highly soluble, but its high concentration solution as described above also does not form precipitates and become turbid even under cold storage (10° C. or less) for a long period. In the present invention, "solubility" is defined as the maximum amount (g) of a solute that can dissolve in 100 ml of water at 25° C., and expressed as the amount (mg) of isoflavones.

The isoflavone-containing composition of the present invention may contain a solubilizing agent such as cyclodextrin or starch octanylsuccinate to solubilize insoluble substances, or may contain a hydrophilic saccharide compound to allow binding of the saccharide compound with isoflavones in the composition by the action of glycosyltransferase or the like. However, addition of such additives is not essential and it is preferable to avoid adding such additives. This is because the proportion of isoflavones in the total solid content of the resulting composition is decreased when such additives are added, and the resulting composition hardly dissolves unless it is heated due to the low solubility of cyclodextrin at room temperature when the composition contains cyclodextrin.

Accordingly, if a solubilizeing agent is added, it is preferable that the amount added is less than the amount of isoflavones contained in the isoflavone-containing composition.

The isoflavone-containing composition of the present invention described above is a composition containing a high concentration of isoflavones and having high solubility, and is also a novel natural material that requires no addition of any solubilizing agents and no chemical modifications. It has not been elucidated yet a reason why the isoflavone-containing composition of the present invention has high solubility in spite of the fact that the composition contains a high concentration of isoflavones that are naturally poorly soluble in water. In other words, the solubilizing mechanism has not been elucidated yet. However, it seems that the coexistence of a specified amount of components other than saponins and isoflavones contained in soybean hypocotyls result in some interaction with isoflavones and thereby isoflavones become highly soluble.

Aspects of a process for producing the isoflavone-containing composition of the present invention will be described hereinafter.

(Starting Material for Extraction)

The starting material for extracting the isoflavone-containing composition of the present invention is not limited and includes whole soybean, defatted soybean, isolated soybean protein, soybean curd refuse (okara) and the like. Preferably soybean hypocotyls are used. The isoflavone content of soybean hypocotyls is 1 to 2% by weight of the total solid content, which is 10 times or more as much as that of soybean seeds. Thus, soybean hypocotyls are a preferable material for obtaining an isoflavone-containing composition with high purity, and are also important for obtaining an isoflavone-containing composition with high solubility. Although the relation between solubility and saponin composition is unknown, the proportion of group A saponins in the total saponins of soybean hypocotyls is 60% by weight or more and the proportion of group B saponins is lower. Such saponin composition (the ratio of group A:group B) in soybean hypocotyls is different from that in soybean cotyledons. A method for preparing soybean hypocotyls is not particularly limited and for example, they may be readily separated by removing the surface skins of soybeans and then roughly crushing them. Preferably, the soybean hypocotyls thus obtained may be sieved to enhance the purity of hypocotyls. Alternatively, commercially available products sold as "soybean hypocotyls" or "soybean germs" may be used. Soybean hypocotyls may be subjected to a pretreatment such as a heating treatment for the purpose of improving the flavor or the like. However, malonyl isoflavone glycosides may be converted into free glycosides by heating, and in this case, it is difficult to separate isoflavones from other components such as saponins. Therefore, it is preferable to use raw soybean hypocotyls or soybean hypocotyls after a slight heat treatment. Full-fat soybeans or defatted soybeans may be also used. However, they have a low isoflavone content, so that it costs time and money to attain the desired purity of isoflavone. Therefore, soybean hypocotyls are preferred.

(Extraction Solvent)

As a solvent for extracting isoflavones from soybean hypocotyls, an aqueous alcoholic organic solvent such as ethanol, methanol or propanol may be used. In view of use in foods, ethanol is preferably used. The alcohol concentration of an extraction solvent is preferably 15 to 95% by volume, more preferably 30 to 90% by volume, still more preferably 40 to 85% by volume, and most preferably 60 to 80% by volume. When the alcohol concentration is too low, isoflavones are difficult to extract and the yield of isoflavones decreases, and in addition, isoflavone glycosides such as daidzin and genistin and malonyl isoflavone glycosides tend to be converted into isoflavone aglycones such as daidzein and genistein during extraction by the effect of β-glucosidase that is naturally contained in soybean hypocotyls, so that it is difficult to obtain an isoflavone-containing composition with high solubility. When the alcohol concentration is too high, the yield of isoflavones decreases and in addition, the production cost increases. Therefore, an alcohol solution with such high concentration is inappropriate.

(Extraction Temperature)

In the present invention, it is important that the extract temperature is 10 to 50° C., more preferably 20 to 40° C. It is needless to say that extraction may be performed at room temperature as long as the room temperature is within the above-described temperature range. When the extraction temperature is too low, the extraction efficiency decreases. On the contrary, when the extraction temperature is too high, malonyl isoflavone glycosides are thermally decomposed and then converted into free isoflavone glycosides, so that it is difficult to obtain an isoflavone-containing composition with high solubility at 25° C. Isoflavones in the form of solution containing isoflavones at high concentration can be recovered from hypocotyls as the starting material in a high yield of 80% or more by extraction with the specified concentration of a solvent and at the specified temperature as described above, depending on extraction conditions. The extraction step described above is preferably repeated more than once to enhance the yield of isoflavones.

(Adsorbent Treatment)

An isoflavone-containing composition having high solubility and containing a high concentration of isoflavones is purified from the crude extract of isoflavones obtained by the extraction step described above. A first purification step comprises dissolving the crude extract in water, if necessary, and bringing the crude extract into contact with a nonpolar adsorbent resin. Since the extract obtained by the extraction step described above contains alcohol, it is preferably subjected to pretreatment such as alcohol removal and concentration, if necessary. Since lipids contained in the starting material may be extracted when the alcohol concentration of an extraction solvent is high, the starting material or the extract may be defatted. A nonpolar adsorbent resin to be used includes preferably nonpolar synthetic adsorbent resins such as HP-20 (manufactured by Mitsubishi Chemical Co.), SP-825 (manufactured by Mitsubishi Chemical Co.), Amberlite XAD-2 and KAD-4 (manufactured by Rohm and Haas Co.), and Duolite S-861 and S-862 (manufactured by Sumitomo Chemical Industry Co.), which are porous styrene-divinylbenzene resins. Duolite C26A (manufactured by Sumitomo Chemical Industry Co.), which is a polar cation exchange resin, and WA-30 (manufactured by Mitsubishi Chemical Co.), which is an anion exchange resin, are not suitable because they do not adsorb isoflavones or the resulting isoflavone material is low soluble. This adsorbent treatment may be achieved batchwise by putting the adsorbent rein in a tank, or may be achieved by filling a column with the adsorbent resin. It is preferable to allow a solution of the crude extract in water to pass through a resin column filled with the resin, from the viewpoint of production efficiency and productivity.

(Elution of Isoflavone-containing Composition)

Next, a specified isoflavone is selectively eluted and collected from a fraction adsorbed to the adsorbent resin with an aqueous alcoholic organic solvent. The aqueous alcoholic organic solvent is preferably aqueous ethanol. In the present invention, it is important that the ethanol concentration of an elution solvent is 15 to 40% by volume, more preferably 20 to 35% by volume. When the ethanol concentration is too low, it requires a large volume of the solvent to collect an isoflavone-containing composition and isoflavones are poorly eluted, so that the isoflavone concentration in the resulting composition decreases. When the ethanol concentration is too high, a large quantity of impurities other than isoflavones such as saponins is eluted, so that the isoflavone purity in the resulting composition decreases, and in addition, nonpolar substances with low-water solubility such as isoflavone aglycones are also eluted, so that an isoflavone fraction with high solubility can not be obtained.

(Processing of Isoflavone-containing Composition)

After the isoflavone-containing composition obtained by the production method described above is heated, evaporated under reduced pressure to remove the organic solvent and then concentrated, the concentrate may be used as it is as an "isoflavone extract" or may be powdered by spray drying, freeze drying or the like. The isoflavone-containing composition thus obtained is a novel isoflavone-containing composition containing a high concentration of isoflavones and having extreme high solubility, wherein the isoflavone content is 25 to 95% by weight of the total solid content and the water solubility at 25° C. is at least 20 mg/100 ml based on the amount of isoflavones.

(Acid Precipitation Treatment)

The isoflavone-containing composition obtained by the above method can be used as it is within the concentration range usually used, for example, in 20 mg/100 ml based on the amount of isoflavones. However, when the isoflavone-containing composition is added to acidic food or beverage in high concentration, the isoflavone-containing composition may be previously subjected to pH adjustment to the acid range followed by removal of insoluble substances generated (for example, proteins) to enhance the transparency of the solution. Edible inorganic acid or organic acid may be used for the pH adjustment, and for example, hydrochloric acid, sulfuric acid, phosphoric acid, acetic acid, malic acid, citric acid or ascorbic acid may be used. The pH of the isoflavone-containing composition may be adjusted to the pH or lower of food or beverage to which the composition is added, usually pH 4 or less, preferably pH 3.5 or less. Then, the isoflavone-containing composition may be maintained at the acidic pH for a given period of time. During all that time, the composition is maintained suitably at room temperature or below, preferably at 10° C. or below. An extract of soybean hypocotyls or the like usually contains proteins as well as isoflavones. When the proteins in the extract are precipitated under acidic conditions, their precipitation tends to be accompanied by precipitation of isoflavones (coprecipitation). In the present invention, however, the coprecipitation is prevented because the protein content of the isoflavone-containing composition of the present invention is decreased by extraction with an alcohol and purification with an adsorbent resin. Isoflavones may be separated from insoluble substances by a conventional solid-liquid separation method such as filtration and centrifugation.

(Elution of Saponin-containing Fraction)

In the present invention, after eluting an isoflavone-containing fraction from a nonpolar adsorbent resin with 15 to 40% by volume aqueous ethanol, a fraction mainly comprising saponins remains adsorbed to the resin. The saponin-containing fraction can be eluted with a higher concentration of alcohol, preferably 60 to 95% by volume, more preferably 65 to 90% by volume aqueous ethanol to obtain a saponin-containing composition containing saponins in an amount of 40% by weight or more of the total solid content. As described above, an isoflavone fraction containing a high concentration of isoflavones and having high solubility, and a saponin fraction containing a high concentration of saponins can be efficiently separated by obtaining an extract at the specified temperature, allowing the extract to be adsorbed to a nonpolar adsorbent resin and then eluting the fractions from the resin with different concentrations of aqueous alcohol solutions, and thereby a saponin material containing a high concentration of saponins can be provided.

(Applicability to Foods)

By adding only a small amount of the isoflavone-containing composition thus obtained to all kinds of edible compositions such as medicines, foods and beverages, a large amount of isoflavones can be provided to those who ingest said edible compositions, because the isoflavone-containing composition contains a high concentration of isoflavones. Moreover, since saponins are contained together in the isoflavone-containing composition, both ingredients of isoflavones and saponins can be effectively ingested. Since the isoflavone-containing composition is highly soluble, it is particularly effective in liquid medicines and foods, and beverages. The isoflavone-containing composition can be provided in solid form such as a tablet or a granule. The isoflavone-containing composition can be also provided in concentrate form such as a portion by taking advantage of its high solubility, and therefore can be used as an ingredient of seasonings such as jams and sauces.

In the present invention, analysis of isoflavones was performed according to a standard method for analysis of soybean isoflavone foods by Japan Health Food and Nutrition Food Association. Saponins were quantified by thin layer chromatography as described hereinbelow, and proteins were quantified by Kjeldahl method.

(Quantification Method of Isoflavone)

A sample corresponding to 1 to 10 mg of isoflavones was precisely weighed, and 25 mL of 70% (v/v) ethanol was added to the sample. After extraction with stirring for 30 minutes at room temperature, the extract was centrifuged. The residue was further extracted twice in the same way as in the above. Extract solutions from three extractions in total were combined, adjusted to a volume of 100 mL with 70% (v/v) ethanol, and then filtered with a 0.45 μm PVDF filter to obtain a test solution. In a confirmatory test of isoflavones, the peaks of the test solution were confirmed at about the same retention times as compared with 12 kinds of standard samples, namely, daidzin, genistin, glycitin, daidzein, genistein, glycitein, malonyl daidzin, malonyl genistin, malonyl glycitin, acetyl daidzin, acetyl genistin and acetyl glycitin (all manufactured by Waco Pure Chemical Industries, Inc.). In a quantitative test, the concentrations of 12 isoflavones in the test solution were quantified (as equivalent converted into daidzin) using daidzin standard samples as standard. The true isoflavone concentrations were calculated by multiplying the obtained values by the following quantification constants: daidzin (1.000), genistin (0.814), glycitin (1.090), malonyl daidzin (1.444), malonyl genistin (1.095), malonyl glycitin (1.351), acetyl daidzin (1.094), acetyl genistin (1.064), acetyl glycitin (1.197), daidzein (0.583), genistein (0.528), and glycitein (0.740). The total amount of isoflavones was determined from the sum of the concentrations of all isoflavones. HPLC conditions of the test solutions and the standard solutions are shown in Table 1.

TABLE 1

| | HPLC Conditions |
|---|---|
| (Column) | YMC-Pack ODS-AM-303 (4.6 × 250 mm) |
| (Mobile phase) | (Solution A) acetonitrile:water:acetic acid = 15:85:0.1 (v/v/v) |
| | (Solution B) acetonitrile:water:acetic acid = 35:65:0.1 (v/v/v) |
| | (Solution A → solution B) linear concentration gradient (50 minutes) |
| (Flow rate) | 1.0 mL/min |
| (Temperature) | 25° C. |
| (Detection) | UV 254 nm |
| (Injection volume) | 10 μL |

(Quantification of Saponin)

A sample was precisely weighed, extracted with stirring for 1 hour with methanol, and then centrifuged to obtain an extract solution. This procedure was repeated again. The resulting extract solutions were combined, and the volume of the combined solution was adjusted to a given volume. This sample solution was spotted on a thin layer chromatography (TLC) plate. The Rf value of the sample spot was compared with that of a saponin standard to confirm that there was the saponin spot on the sample. An integration value of the spot area was determined using a standard line previously prepared by using a saponin standard, and thereby the amount of saponins was calculated. The conditions of thin layer chromatography are shown in Table 2.

TABLE 2

| | TLC conditions |
|---|---|
| (TLC plate) | Silica gel plate 60F254 (thickness 0.25 mm, manufactured by Merck Co.) |
| (Development solvent) | chloroform:methanol:water (bottom layer of 65:25:10 (v/v/v) solution) |
| (Development) | 18 cm |
| (Detection) | heating at 105° C. for 15 minutes after spraying 10% sulfuric acid solution |

EXAMPLES

Hereinafter, the present invention is illustrated by reference to Examples which do not restrict the technical scope of the present invention.

Example 1

To 500 g of raw soybean hypocotyls was added 2.0 L of 70% by volume aqueous ethanol, and the mixture was extracted with stirring at 30° C. for 8 hours. After the extract solution was separated by filtration, the residue was extracted again with 2.0 L of 70% by volume aqueous ethanol in the same way as in the above. The two extract solutions were combined.

The combined extract solution was concentrated under reduced pressure at 40° C. to completely remove the organic solvent. The crude extract thus obtained was dissolved in water, and applied at SV2 onto a column (100 mL) filled with a nonpolar synthetic adsorbent resin, Diaion HP-20 (manufactured by Mitsubishi Chemical Co.). Then, the column was eluted with 30% by volume aqueous ethanol to obtain an isoflavone fraction. The fraction was concentrated under reduced pressure at 40° C., dried and powdered to obtain 15 g of an isoflavone-containing composition. The concentration of isoflavones in the obtained isoflavone-containing composition was 48.0% based on the weight of the total solid content. The composition also contained 23.8% of saponins and 14.1% of proteins.

Experiment Example 1

Investigation of the Concentration of Ethanol in an Extraction Solvent

Soybean hypocotyls were subjected to extraction in the same way as in Example 1 except that the ethanol concentration of an extraction solvent was changed as shown in Table 3, and changes in the relative proportions of isoflavones in the resulting extract and in the yield of isoflavones from soybean hypocotyls were examined. The results are shown in Table 3.

TABLE 3

Relative proportions of isoflavones in ethanol extract solutions and yields of isoflavones

| | Ethanol concentration (% by volume) | | | | | | |
|---|---|---|---|---|---|---|---|
| | 10 | 20 | 40 | 50 | 70 | 90 | 100 |
| Mal-ISO | 18.0 | 65.3 | 60.3 | 59.6 | 55.3 | 45.3 | 28.6 |
| Ac-ISO | 6.3 | 2.1 | 6.3 | 4.1 | 3.3 | 0.0 | 0.0 |
| ISO | 23.7 | 20.6 | 31.1 | 33.0 | 36.3 | 46.6 | 64.3 |
| Agl | 52.0 | 12.0 | 2.3 | 3.3 | 5.1 | 8.1 | 7.1 |
| Yield of isoflavones (%) | 63 | 76 | 82 | 82 | 86 | 38 | 10 |

* Mal-ISO: malonyl isoflavone glycoside
Ac-ISO: acetyl isoflavone glycoside
ISO: isoflavone glycoside
Agl: isoflavone aglycone When the ethanol concentration of an extract solvent was 10% by volume, the yield of isoflavones was decreased, the content of isoflavone aglycones was increased, and the content of malonyl isoflavone glycosides was rapidly decreased. This is probably because β-glucosidase in soybean hypocotyls reacted with malonyl isoflavone glycosides due to the low concentration of ethanol and thereby the malonyl isoflavone glycosides were decomposed to aglycones. When the ethanol concentration was 100% by volume, the yield of isoflavones was rapidly decreased, the content of isoflavone glycosides was increased, and the content of malonyl isoflavone glycosides was rapidly decreased. Accordingly, the concentration of ethanol in an extraction solvent is suitably at least 15 to 95% by volume, more preferably 30 to 90% by volume, more preferably 40 to 85% by volume, most preferably 60 to 80% by volume.

Comparative Example 1

Extraction with Ethanol at High Temperature

To 500 g of raw soybean hypocotyls was added 1.5 L of 70% by volume aqueous ethanol, and the mixture was extracted with heating under reflux at 70° C. for 8 hours. After the extract solution was separated by filtration, the residue was extracted under reflux again with 1.5 L of 70% by volume aqueous ethanol in the same way as in the above. The two extraction solutions were combined.

The combined extract solution was concentrated under reduced pressure at 60° C. to completely remove the organic solvent. The extract thus obtained was dissolved in water, and applied at SV2 onto a column (100 mL) filled with a nonpolar adsorbent resin, HP-20 (manufactured by Mitsubishi Chemical Co.). The column was eluted with 30% by volume aqueous ethanol to obtain an isoflavone fraction. The fraction was concentrated under reduced pressure at 60° C., dried and powdered to obtain 20 g of an isoflavone-containing composition. The isoflavone concentration of the obtained isoflavone-containing composition was 38% based on the weight of the total solid content. The saponin concentration was 18% by weight of the total solid content.

Comparative Example 2

Extraction with High Concentration of Ethanol

An isoflavone fraction was obtained in the same way as in Example 1 except that the concentration of aqueous ethanol used for elution of isoflavones from a column was 70% by volume. The fraction was concentrated under reduced pressure at 60° C., dried and powdered to obtain 30 g of an isoflavone-containing composition. The isoflavone concentration of the obtained isoflavone-containing composition was 20.7% by weight of the total solid content. The saponin concentration was 33% by weight of the total solid content.

Comparative Example 3

Extraction at High Temperature, Anion Resin, and Elution with High Concentration of Ethanol To 500 g of raw soybean hypocotyls was added 1.5 L of 70% by volume aqueous ethanol, and the mixture was extracted with heating under reflux at 70° C. for 8 hours. After the extract solution was separated by filtration, the residue was extracted under reflux again with 1.5 L of 70% by volume aqueous ethanol in the same way as in the above. The two extract solutions were combined.

The combined extract solution was concentrated under reduced pressure at 60° C. to completely remove the organic solvent. The extract thus obtained was dissolved in water, and applied at SV2 onto a column (100 mL) filled with an anion exchange resin, WA-30 (manufactured by Mitsubishi Chemical Co.). Then, the column was eluted with 70% by volume aqueous ethanol to obtain an isoflavone fraction. The fraction was concentrated under reduced pressure at 60° C., dried and powdered to obtain 6 g of an isoflavone-containing composition. The isoflavone concentration of the obtained isoflavone-containing composition was 75% based on the weight of the total solid content. The saponin concentration was 0.5% by weight of the total solid content.

The relative proportions of isoflavones in the isoflavone-containing compositions obtained in Example 1 and Comparative Examples 1 to 3 are shown in Table 4. The isoflavone-containing composition obtained in Example 1 had a high proportion of malonyl isoflavone glycosides and low proportions of isoflavone glycosides and isoflavone aglycones, as compared with those in the isoflavone-containing compositions obtained in Comparative Examples 1 to 3. The reason why the proportion of malonyl isoflavone glycosides was decreased in Comparative Example 1 was probably that malonyl isoflavone glycosides were decomposed to isoflavone glycosides by raising the extraction temperature to 70° C. The reason why the proportion of malonylisoflavone glycosides was decreased in Comparative Example 2 was probably that a large amount of components other than malonyl isoflavone glycosides were eluted by increasing the concentration of ethanol used for elution.

TABLE 4

(Unit: %)

|  | Example 1 | Comp. Example 1 | Comp. Example 2 | Comp. Example 3 |
|---|---|---|---|---|
| (condition) | | | | |
| Ethanol Concentration for Extraction | 70% | 70% | 70% | 70% |
| Ethanol Concentration for Elution | 30% | 30% | 70% | 70% |
| Extraction Temperature | 30° C. | 70° C. | 30° C. | 70° C. |
| Kind of Resin | Nonpolar adsorbent | Nonpolar adsorbent | Nonpolar adsorbent | Anion-exchange |
| (Relative proportions of Isoflavones) | | | | |
| Malonyl glycoside | 68.3 | 19.8 | 30.3 | 0.3 |
| Acetyl glycoside | 8.8 | 7.6 | 5.5 | 0.9 |
| Free glycoside | 22.8 | 67.6 | 53.8 | 98.5 |
| Aglycone | 0.1 | 5.0 | 10.4 | 0.3 |

Comparative Example 4

Preparation of Soluble Isoflavones Using Cyclodextrin

In 500 ml of 50% aqueous ethanol at 80° C., 5 g of the isoflavone-containing composition obtained in Comparative Example 1 (extraction with high concentration of ethanol) and 25 g of β-cyclodextrin (manufactured by Nihon Shokuhin Kako Co.) were dissolved, and the solution was stirred at 80° C. for 3 hours. The solution was then left at room temperature overnight. The supernatant was dried under reduced pressure to obtain 10 g of powder. The concentration of isoflavones in the isoflavone-containing composition thus obtained was 8.4% based on the weight of 15 the total solid content. The concentration of saponins was 1.8% by weight of the total solid content.

Experiment Example 2

The isoflavone-containing compositions obtained in Example 1 and Comparative Examples 1 to 4 were dissolved in water at pH 7.0 at 25° C. with stirring so that the isoflavone concentration is 20 mg/100 ml. After stirring, the solubility was evaluated. The stability after cold storage at 4° C. for 2 weeks was also evaluated. The results are shown in Table 5.

TABLE 5

|  | Example | Comparative Example | | | |
|---|---|---|---|---|---|
|  | 1 | 1 | 2 | 3 | 4 |
| Ethanol Concentration for Extraction (%) | 70 | 70 | 70 | 70 | 70 |
| Extraction Temperature (° C.) | 30 | 70 | 30 | 70 | 30 |
| Ethanol Concentration for Elution (%) | 30 | 30 | 70 | 70 | 70 |
| Isoflavone Content (dry %) | 48 | 38 | 20.7 | 75 | 8.4 |
| Malonyl isoflavone glycoside Content (dry %) | 32.8 | 7.5 | 6.3 | 0.2 | 0.7 |
| Saponin Concentration (dry %) | 24 | 18 | 33 | 0.5 | 1.8 |
| Solubility after stirring (25° C.) | ○ | x | x | x | x |
| Stability after 2 weeks' cold storage | ○ | x | x | x | x |

(Evaluation criteria)
○: no precipitate and no turbidity were observed.
x: precipitates or turbidity was observed.

As shown in Table 5, in Example 1, the isoflavone percentage in the total solid content was as high as 48% and the solubility at 25° C. was also extremely high. In Example 1, the stability after cold storage for 2 weeks was also extremely good. Therefore, an isoflavone-containing composition having a high concentration of isoflavones and having extreme high water solubility could be obtained under the conditions of Example 1. The maximum amount (solubility) of the isoflavone-containing composition obtained in Example 1 that could dissolve in water at 25° C. was surprisingly at least 1,000 mg/100 ml based on the amount of isoflavones.

In Comparative Example 1, although the isoflavone content was as high as 38%, both of the solubility at 25° C. and the stability after cold storage were poor. This was probably because naturally water-insoluble substances including isoflavone aglycones, isoflavone glycosides and pigments were extracted as a result of extraction with heating under reflux at a high temperature (70° C.).

In Comparative Example 2, the isoflavone content was as low as 20% and the solubility at 25° C. was also poor. This was probably because a large amount of poorly water-soluble nonpolar substances was eluted from the adsorbent resin by using a high concentration of aqueous ethanol for elution of an isoflavone fraction.

Although the isoflavone content was as high as 75% in the isoflavone-containing composition obtained in Comparative Example 3, the composition did not dissolve at all in water at 25° C. This was probably because the solubility of isoflavones itself was naturally as low as about 5 mg/L and could not be improved by high degree of purification.

In Comparative Example 4, the isoflavone content was as low as 8.4% because the percentage of saccharides in the total solid content was increased as a result of inclusion of isoflavones with cyclodextrin. The obtained isoflavone-containing composition did not dissolve at all in water at 25° C. This was probably because the solubility of the obtained composition depended on that of cyclodextrin and cyclodextrin did not dissolve in water at 25° C. In order to dissolve the composition, heating at 80° C. for 10 minutes or more was needed.

As seen from the above-described results, only in Example 1, that is, in the case of combining extraction and elution with the specified concentration of ethanol, and extraction at the specified temperature, an isoflavone-containing composition having high purity, high solubility and good stability under cold storage could be obtained. The relative proportions of components of the composition having such excellent properties were examined. As a result, it has been found that it is important that: (1) the content of isoflavones is as high as 25% by weight or more of the total solid content; (2) the content of malonyl isoflavone glycosides is 15 to 95% by weight, more preferably 30 to 90% by weight, still more preferably 35 to 85% by weight, most preferably 35 to 80% by weight, by taking the sum of the total amounts of isoflavones and saponins as 100% by weight; (3) the content of isoflavones other than malonyl isoflavone glycosides is 0 to 50% by weight, more preferably 0 to 45% by weight, still more preferably 0 to 40% by weight, most preferably 0 to 35% by weight, by taking the sum of the total amounts of isoflavones and saponins as 100% by weight; and (4) the content of saponins is 5 to 60% by weight, more preferably 10 to 50% by weight, still more preferably 15 to 45% by weight, most preferably 20 to 40% by weight, by taking the sum of the total amounts of isoflavones and saponins as 100% by weight.

Example 2

In 100 ml of water, 5 g of the isoflavone-containing composition obtained in Example 1 was dissolved, and the solution was adjusted to pH 3.0 with citric acid. After allowing the solution to stand overnight at room temperature, the solution was centrifuged at 3000 g for 10 minutes and the supernatant was collected. The supernatant was adjusted to pH 6.5 with sodium hydrogen carbonate, dried and powdered to obtain 4 g of powder. The isoflavone concentration of the isoflavone-containing composition thus obtained was 37% by weight of the total solid content. The isoflavone-containing composition thus obtained had extreme high solubility in the neutral range (pH 7.0) and even in the acid range (pH 3.0), which is at least 100 mg/100 ml based on the amount of isoflavones. In addition, no precipitate and no turbidity were observed in the composition after cold storage for 2 weeks. Therefore, an isoflavone-containing composition having high solubility and good stability under cold storage was obtained.

Example 3

Isoflavone-containing Beverage

The isoflavone-containing composition obtained in Example 1 was compounded using the combination ratio shown in Table 6, and then UHT sterilized to prepare a beverage.

TABLE 6

| | |
|---|---|
| Isoflavone-containing composition | 0.17 g |
| Sugar | 16.0 g |
| Grapefruit juice | 1.3 g |
| Acidulant | 1.0 g |
| Calcium lactate | 0.8 g |
| Vitamin D3 | 100 IU |
| Grapefruit flavor | 0.1 g |
| Water | 80.63 g |
| Total | 200.0 g |

The beverage had high solubility, good appearance and good flavor. Drinking 50 mL of the beverage can provide intake of 40 mg of isoflavones.

Example 4

Production of Isoflavone-containing Portion Beverage

The isoflavone-containing composition obtained in Example 2 was compounded using the combination ratio shown in Table 7, sterilized and then aseptically packed to produce portions (10 g×15).

TABLE 7

| | |
|---|---|
| Isoflavone-containing composition | 1.5 g |
| Sugar | 40.0 g |
| Fruit juice | 10.0 g |
| Citric acid | 5.0 g |
| Flavor | 0.5 g |
| Water | 94.5 g |
| Total | 150.0 g |

The portion thus obtained had good appearance, and had good flavor when the portion was diluted with 100 ml of water. Consuming one pack of this portion can provide intake of 40 mg of isoflavones. The portion is also excellent in portability.

INDUSTRIAL APPLICABILITY

According to the present invention, application of isoflavones can be remarkably expanded in all kinds of foods including beverages in which isoflavones are required to be readily soluble in water even at low temperature, as well as in pharmaceuticals and cosmetics. Particularly, the present invention can greatly contribute to industry relating to health foods in which various physiological functions of isoflavones are utilized.

The invention claimed is:

1. An isoflavone-containing composition which comprises 15 to 95% by weight of malonyl isoflavone glycosides, 0 to 50% by weight of isoflavones other than malonyl isoflavone glycosides and 5 to 60% by weight of saponins, by taking the sum of the total amounts of isoflavones and saponins in said composition as 100% by weight, wherein the proportion of group A saponins in the saponins is 55% by weight or more, by taking the total amount of saponins in the composition as 100% by weight, and the composition contains isoflavones in an amount of 25 to 95% by weight of the total solid content.

2. The isoflavone-containing composition according to claim 1, which is prepared from soybean hypocotyls as the starting material.

3. The isoflavone-containing composition according to claim 1, which has a water solubility of at least 20 mg/100 ml at 25° C. based on the amount of isoflavones.

4. A process for producing the isoflavone-containing composition according to claim 2, which comprises the steps of:
   (A) extracting soybean hypocotyls with 15 to 95% by volume aqueous ethanol at 10 to 50° C. to obtain an extract;
   (B) bringing a solution of the extract obtained by the step (A) in water into contact with a nonpolar adsorbent resin to allow isoflavones to be adsorbed to the resin; and
   (C) eluting isoflavones from the adsorbent resin with 15 to 40% by volume aqueous ethanol.

5. An edible composition containing the isoflavone-containing composition according to claim 1.

6. A process for fractionating isoflavones and saponins, which comprises extracting soybean hypocotyls with 15 to 95% by volume aqueous ethanol at 10 to 50° C. to obtain an extract, bringing a solution of the extract in water into contact with a nonpolar adsorbent resin, eluting an isoflavone-containing fraction from the adsorbent resin with 15 to 40% by volume aqueous ethanol, and then eluting a saponin-containing fraction from the adsorbent resin with 65 to 90% by volume aqueous ethanol.

* * * * *